US006987203B2

(12) United States Patent
Ancel

(10) Patent No.: US 6,987,203 B2
(45) Date of Patent: Jan. 17, 2006

(54) PROCESS FOR THE PREPARATION OF PHYTONE

(75) Inventor: Jean-Erick Ancel, Saint Genis Laval (FR)

(73) Assignee: Adisseo France S.A.S., Antony (FR)

( * ) Notice: Subject to any disclaimer, the term of this patent is extended or adjusted under 35 U.S.C. 154(b) by 3 days.

(21) Appl. No.: 10/500,285

(22) PCT Filed: Jan. 13, 2003

(86) PCT No.: PCT/EP03/00231

§ 371 (c)(1),
(2), (4) Date: Aug. 6, 2004

(87) PCT Pub. No.: WO03/057654

PCT Pub. Date: Jul. 17, 2003

(65) Prior Publication Data

US 2005/0065380 A1    Mar. 24, 2005

(30) Foreign Application Priority Data

Jan. 14, 2002 (EP) ................................ 02356006

(51) Int. Cl.
  *C07C 45/72*  (2006.01)
  *C07C 45/73*  (2006.01)
  *C07C 49/04*  (2006.01)

(52) U.S. Cl. ...................... 568/391; 568/396; 568/398; 568/415

(58) Field of Classification Search ................ 568/391, 568/396, 398, 415

See application file for complete search history.

(56) References Cited

U.S. PATENT DOCUMENTS

| | | | |
|---|---|---|---|
| 3,867,408 A | | 2/1975 | Dietl et al. ............... 260/340.9 |
| 3,917,710 A | * | 11/1975 | Pond et al. .................. 568/386 |
| 4,292,459 A | * | 9/1981 | Cardenas et al. ............ 585/641 |
| 4,693,849 A | * | 9/1987 | Mignani et al. ............. 260/404 |
| 5,449,844 A | * | 9/1995 | Ancel et al. ................. 568/691 |
| 6,232,506 B1 | * | 5/2001 | Kido et al. .................. 568/390 |

FOREIGN PATENT DOCUMENTS

| | | | |
|---|---|---|---|
| EP | 0 544 588 A1 | | 6/1993 |
| EP | 1179520 | * | 2/2002 |

OTHER PUBLICATIONS

Mignani et al. Synthesis of new unsaturated enynes, catalysed by copper (I) complexes. ▫▫Tetrahedron Letters, vol. 31 (36) p 5161-5164, 1990.*

* cited by examiner

*Primary Examiner*—Sikarl A. Witherspoon
(74) *Attorney, Agent, or Firm*—Oliff & Berridge, PLC

(57) ABSTRACT

A process for the preparation of a novel intermediate compound useful in the preparation of phytone and vitamin E.

13 Claims, No Drawings

PROCESS FOR THE PREPARATION OF PHYTONE

The present invention relates to a process for the preparation of intermediate compounds useful in the preparation of phytone and/or Vitamin E.

Vitamin E has been prepared chemically for a long time using many various processes. In general, this vitamin is prepared from an intermediate compound known as phytone which has the following chemical structure

PHYTONE

European Patent 0544588 discloses a process for the production of Vitamin E through the condensation of a polyunsaturated allyl alcohol derivative. U.S. Pat. No. 3,867,408 discloses the preparation of novel ketal compounds which may be used in the preparation of phytone which in turn is an intermediate in the production of Vitamin E.

We have now synthesised a novel compound which can be used as an intermediate compound in the synthesis of phytone and if desired in the synthesis of Vitamin E.

Accordingly, the present invention provides a process for the preparation of a compound of formula (I)

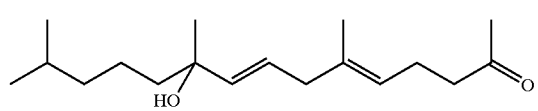
(I)

which comprises reacting a compound of formula (II)

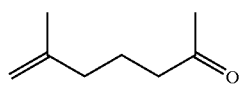
(II)

with a compound of formula (III)

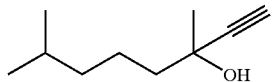
(III)

in the presence of a catalyst and a polar solvent.

Compound (I) is a novel compound and forms another aspect of the present invention.

The process for the preparation of compound (I) is carried out in the presence of a polar solvent. Suitable solvents include aprotic polar solvents such as dimethylacetamide, dimethylformamide, N-methyl pyrrolidone and di-methyl sulfoxide. The preferred solvent is dimethylacetamide. The solvent may be present in a concentration of from 0.01 and 5 mol/l, preferably from 0.1 to 1 mol/l.

Although not essential, water may be added to the solvent. Where water is added to the solvent, the concentration of water is suitably from 10 to 50% in volumetric parts.

The process is carried out in the presence of a catalyst. Suitable catalysts include cationic divalent ruthenium complexes. The preferred catalyst is cyclopentadienyl ruthenium hexafluorophosphate tris-acetonitrile.

A preferred embodiment of the present invention comprises the addition of the reactants to a solution of the catalyst. This process is preferred in order to inhibit degradation of the reactants.

The process may also be carried out in the presence of a second solvent which is immiscible with the polar solvent. Solvents fulfilling this condition include apolar solvents. Suitable apolar solvents include aromatic hydrocarbons such as toluene, benzene and xylene; and aliphatic hydrocarbons such as pentane, heptane, hexane and octane; and monophase mixtures of a hydrocarbon solvent and an ether. The second solvent may be present in a volumetric ratio of from 0.01 to 10, preferably from 0.5 to 2, compared to the catalyst polar phase.

The process may be carried out at a temperature of from 20 to 100° C., preferably from 20 to 60° C. and under atmospheric or elevated pressure. Preferably, the reaction is carried out under atmospheric pressure.

Compound (III) is preferably added slowly to the reaction medium to avoid the formation of side—reaction products.

The compounds of formula (I), obtained by the process according to the present invention, is particularly suitable for use as a starting material in the synthesis of phytone. Thus, according to another aspect of the present invention there is provided a process for the preparation of phytone which comprises (a) a first step of hydrolysing the following compound

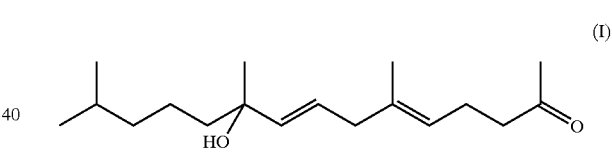
(I)

to produce a hydrolysis product; and (b) a second step of hydrogenating said hydrolysis product.

The first step of this process, namely the hydrolysis step, is suitably carried using an acid catalyst such as sulphonic acid, sulphuric acid or hydrogen chloride. The catalyst may be present in an amount of from 0.001 to 0.5 molar equivalents, preferably between 0.05 and 0.1 molar equivalents, compared to the compound of formula (I).

The hydrolysis is also suitably carried out in the presence of an organic solvent such as toluene or an ether, for example diethyl ether or tetrahydrofuran. The temperature of the reaction may be between −50 and +150° C., preferably between 20 and 100° C.

The product of the hydrolysis step is then hydrogenated. The hydrogenation is suitably carried out in the presence of hydrogen gas and in the presence of a metal or metal salt. Suitable metals and metal salts include Raney nickel (a nickel/aluminium alloy) optionally in the presence of iron, manganese, cobalt, copper, zinc or chromium; zinc in the presence of acetic acid; stannous chloride; and molybdenum (III) salts. The reaction may also be carried out in the presence of palladium or platinum which may be supported on an suitable inert support such as charcoal. The hydrogenation is preferably carried out in the presence of palladium on an inert support such as on charcoal. The amount of metal or metal salt employed is generally from 0.01 to 3 molar equivalents, preferably from 0.05 to 2 molar equivalents.

The hydrogenation step is generally conducted in a solvent which may be selected from alcohols such as methanol or ethanol; linear or cyclic ethers e.g. tetrahydrofuran; and aromatic hydrocarbons. The preferred solvent is an ether, especially tetrahydrofuran.

The reaction temperature in the hydrogenation step is generally from 20° C. to 150° C., preferably from 20° C. to 90° C. and under a gas a pressure of 1 to 50 bars, preferably 5 to 10 bars is generally used.

The hydrolysis and hydrogenation may be carried out as two separate steps or combined as one step in the reaction system.

The process for the preparation of phytone is suitably carried out for a period of time from 30 minutes to 24 hours, preferably from 30 minutes to 6 hours under the aforementioned reaction conditions in order to facilitate complete reaction of the reaction compounds.

Vitamin E may synthesised from the phytone made available from the process of the present invention.

The present invention will now be illustrated with reference to the following examples:

EXAMPLE 1

Preparation of Compound (I)

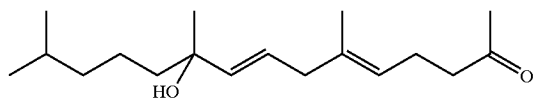
(I)

22 mg of catalyst were dissolved, under argon, in a mixture of 750 microliters of dimethyl acetamide and 250 microliters of water (solution so-called further polar phase). The resulting solution was heated at 60° C. A solution of 1 ml of heptane (containing 63 mg of compound (II) and 77 mg of compound (III) was then slowly added over 90 minutes. The solution was stirred for 3 additional hours at 60° C., and was cooled to 20° C. The heptane phase was separated from the polar phase, and 1 ml of pure heptane was added to the polar phase. The resulting mixture was stirred for 15 minutes at 20° C., and the heptane phase was separated. The procedure was repeated four times: the four heptane phases were collected; the heptane was distilled off, and the remaining oily residue was purified using chromatography on silica gel (Eluent: Pentane/Diethyl ether=2/1 in volume). Pure compound (I) was obtained as a yellow oil. Yield: 84 milligrams (60%).

EXAMPLE 2

Preparation on Phytone

Phytone was prepared in two steps from the compound obtained in Example 1 using the following amounts:

| Compound | Amount | Molar Mass | millimoles |
|---|---|---|---|
| Compound I | 0.689 g | 280 | 2.46 |
| Toluene | 30 ml | 92 | — |
| APTS.H$_2$O | 0.01 g | 190.22 | 0.053 (0.02 eq) |
| Ethanol | 15 ml | 46 | — |
| Pd on C; 5% w/w | 0.117 g | 106.42 | 0.055 (0.02 eq) |

APTS, H$_2$O is para-toluene sulfonic acid, monohydrate

Compound (I), toluene and mono hydrated APTS were placed in a 25 ml round bottom flask and left to react for 3 hours under smooth reflux of toluene. 10 ml of a saturated aqueous solution of sodium carbonate was then added and the resulting product extracted three times with ether. After distillation of ether, the residue obtained was immediately placed in a glass vial containing the palladium-black, and ethanol under an argon atmosphere. The vial was placed in a stainless steel autoclave. The autoclave was sealed shut and purged with hydrogen. The hydrogen pressure was fixed at 5±0.2 bars and the contents agitated. The hydrogenation reaction was continued for 6 hours at ambient temperature. The autoclave was then degassed and contents poured into a little column containing a filtration celite. The column was washed with ethanol and the filtrate concentrated. A weight of 0.587 g of phytone was obtained. The yield of product was 89% with 95% purity.

EXAMPLE 3

Preparation of Phytone

Phytone was prepared in a singe step from the compound obtained in Example 1 using the following amounts:

| Compound | Amount | Molar Mass | millimoles |
|---|---|---|---|
| Compound I | 138 mgg | 280 | 0.493 |
| Tetrhydrofuran | 2 ml | 72 | — |
| Sulphuric Acid (96% in water) | 7 mg | 98 | 0.07 (0.14 eq) |
| Pd on C; 5% w/w | 105 mg | 106.42 | 0.049 0.1 eq Pd) |

The reaction was conducted in a 5 ml glass flask, placed in a stainless steel autoclave, under a pressure of 5 bar of hydrogen, during 1.5 hours at 65° C. (external heating of the autoclave). The autoclave was depressurised, purged with argon and then opened. Analysis if the crude sample, after filtration and treatment with ether and water) revealed a yield of phytone of more than 95%.

What is claimed is:

1. Accordingly, the present invention provides a process for the preparation of a compound of formula (I)

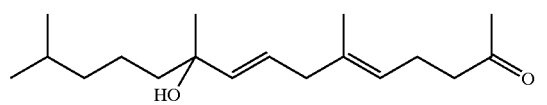
(I)

which comprises reacting a compound of formula (II)

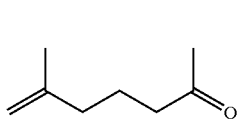

with a compound of formula (III)

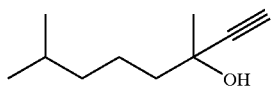

in the presence of a catalyst and a polar solvent.

2. A process as claimed in claim 1 in which the polar solvent is selected from dimethylformamide, dimethylacetamide, dimethylsulfoxyde or N-methyl pyrrolidone.

3. A process as claimed in claim 1 in which the catalyst is selected from cationic divalent ruthenium complexes.

4. A process as claimed in claim 1 carried out in the presence of a second solvent, said second solvent being immiscible with the first solvent.

5. A process as claimed in claim 4 in which the second solvent is an apolar solvent selected from alipahtic or aromatic hydrocarbons.

6. A process as claimed in claim 1 carried out at a temperature of from 20 to 100° C. and under atmospheric pressure.

7. A compound of formula (I) represented by the following structure.

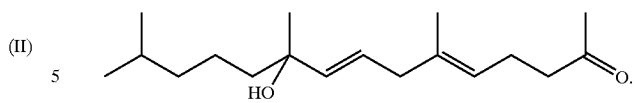

8. A process for the preparation of phytone which comprises (a) a first step of hydrolysing the compound as claimed in claim 7 to produce a hydrolysis product; and (b) a second step of hydrogenating the hydrolysis product of step (a).

9. A process as claimed in claim 8 wherein the first step is carried out in the presence of an acid catalyst selected from sulphonic acid, sulphuric acid and hydrogen chloride.

10. A process as claimed in claim 8 in which the first step is carried out in the presence of an organic solvent selected from an organic hydrocarbon and an ether.

11. A process as claimed in claim 8 in which the second step is carried out in the presence of hydrogen and a metal or metal salt selected from palladium or platinum, Raney nickel optionally in the presence of iron, manganese, cobalt, copper, zinc or chromium; zinc in the presence of acetic acid; stannous chloride; and molybdenum (III) salts.

12. A process as claimed in claim 11 wherein the catalyst is palladium supported on charcoal.

13. A process as claimed in claim 1 wherein the catalyst is selected from the group consisting of cyclopentadienyl ruthenium hexafluorophosphate tris-acetonitrile and pentamethyl-cyclopentadienyl ruthenium hexafluorophosphate tris-acetonitrile.

* * * * *